United States Patent [19]

Nakamura et al.

[11] Patent Number: 5,525,722
[45] Date of Patent: Jun. 11, 1996

[54] PROCESS FOR PRODUCING BIOCOZAMYCIN BENZOATE

[75] Inventors: Hitoshi Nakamura, Mino; Ryoichi Kawakami, Toyonaka; Kunihiko Shiina, Itami, all of Japan

[73] Assignee: Fujisawa Pharmaceutical Co., Ltd., Osaka, Japan

[21] Appl. No.: 495,672

[22] PCT Filed: Jan. 19, 1994

[86] PCT No.: PCT/JP94/00081

§ 371 Date: Jul. 28, 1995

§ 102(e) Date: Jul. 28, 1995

[87] PCT Pub. No.: WO94/17073

PCT Pub. Date: Aug. 4, 1994

[30] Foreign Application Priority Data

Jan. 28, 1993 [JP] Japan .................................. 5-012301

[51] Int. Cl.$^6$ ........................................... C07D 498/08
[52] U.S. Cl. ................................................ 540/456
[58] Field of Search ................................... 540/456

[56] References Cited

U.S. PATENT DOCUMENTS 3,923,790  12/1975  Imanaka et al. .................... 540/456

*Primary Examiner*—Robert T. Bond
*Attorney, Agent, or Firm*—Oblon, Spivak, McClelland, Maier & Neustadt

[57] ABSTRACT

A process for producing bicozamycin benzoate is provided which comprises reacting bicozamycin with benzoic anhydride in the presence of 4-dimethylaminopyridine. The process provided for producing bicozamycin benzoate gives improved yields as compared with the prior art process.

2 Claims, No Drawings

PROCESS FOR PRODUCING BIOCOZAMYCIN BENZOATE

TECHNICAL FIELD

The present invention relates to a novel process for producing bicozamycin benzoate.

BACKGROUND ART

Bicozamycin benzoate is a substance known in the art (cf. e.g. Japanese Kokai Tokkyo Koho Sho 48-39497 and U.S. Pat. No. 3,923,790). It is currently on the market as a fishery drug and under development also as a veterinary drug. The process for producing bicozamycin benzoate as described in the above-cited patent specifications comprises reacting bicozamycin with benzoyl chloride. In said process, the selectivity of the esterification reaction is low and, as a result, the reaction product contains a significant amount of byproducts such as bicozamycin dibenzoate. For commercial production of the objective compound bicozamycin benzoate, said process is thus not fully satisfactory from the yield and production cost viewpoints.

For solving the above problems by attaining an increase in the yield of bicozamycin benzoate, among others, it is crucial to find out a way to increase the selectivity toward monoesterification.

DISCLOSURE OF THE INVENTION

As a result of intensive investigations made by the present inventors to solve the above problems, it was found that the selectivity toward monoesterification can be improved and the yield of bicozamycin benzoate can be much increased when bicozamycin is reacted with benzoic anhydride in the presence of 4-dimethylaminopyridine. Further studies based on this new finding have now led to completion of this invention.

The reaction involved in this invention may be illustrated as follows:

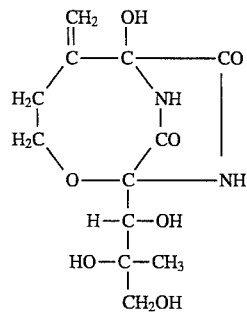

(Bicozamycin)

| 4-Dimethylaminopyridine, benzoic anhydride

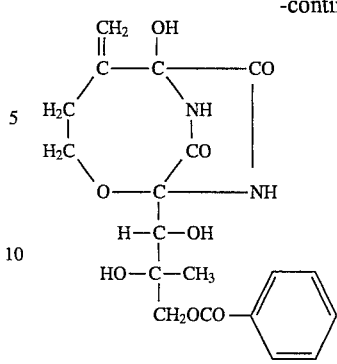

(Bicozamycin benzoate)

This invention consists in reacting bicozamycin with benzoic anhydride in the presence of 4-dimethylaminopyridine. Bicozamycin is the same substance as WS-4545 substance (cf. Japanese Patent Publication Sho 48-29158) produced by a microorganism belonging to the genus Streptomyces (e.g. *Streptomyces sapporonensis* ATCC 21532) and is known in the art. 4-Dimethylaminopyridine is used preferably in a catalytic amount.

This reaction is generally carried out in a solvent. As the solvent, there may be mentioned water, acetone, dioxane, acetonitrile, chloroform, methylene chloride, tetrahydrofuran, ethyl acetate, ether, pyridine, N, N-dimethylacetamide, dimethyl sulfoxide, N, N-dimethylformamide, N-methylpyrrolidone, diglyme, triglyme, hexamethylphosphoramide and other ordinary organic solvents inert to the reaction. Further, the reaction of this invention is preferably performed in the presence of a base such as an alkali metal hydrogen carbonate, a trialkylamine, pyridine or the like. Among such bases, those that are liquid may be used also as solvents. Particularly favorable results may be obtained when this reaction is carried out in pyridine. Although the reaction temperature is not critical, the reaction can be carried out smoothly under cooling or at room temperature in most instances. The reaction product can be isolated, purified and recovered in the conventional manner.

The bicozamycin benzoate production process according to the invention has advantages over the prior art process in that it gives much improved yields of bicozamycin benzoate, that the contents of by-products (bicozamycin dibenzoate, bicozamycin tribenzoate, etc.) in the reaction product is low and that, therefore, the objective substance bicozamycin benzoate can be isolated and purified from the reaction product with ease, for instance. Said process thus remarkably contribute to cost reduction in the commercial production of bicozamycin benzoate.

In the following, the effects of this invention are illustrated by means of a test example.

TEST EXAMPLE (COMPARISON WITH PRIOR ART)

(1) Prior art process (acid chloride process):

A 300-ml three-necked flask was charged with 150 ml of pyridine and 43.8 g (on the pure substance basis) of bicozamycin, and the mixture was stirred at room temperature for about 30 minutes for attaining dissolution. Then, while the liquid temperature was maintained at 20° to 25° C., 57.0 g of benzoyl chloride was added dropwise over about 30 minutes. After completion of the addition, the resultant mixture was further stirred at the same temperature for 1.5 hours and, then, the reaction was terminated by adding 17.5 g of a 20% (w/w) aqueous solution of sodium chloride (% formation of the objective compound: 89.3%). A 1,000-ml three-necked flask was charged with 350 ml of ethyl acetate and 350 ml of water, and the above reaction mixture was added thereto with stirring. The resultant mixture was then allowed to stand for 10 minutes for phase separation into an aqueous layer and an organic layer. The organic layer was separated and concentrated to about 250 ml under reduced pressure. Ethyl acetate (250 ml) was added to the concentrate and the resultant mixture was again concentrated to about 250 ml under reduced pressure. To this concentrate was added 250 ml of ethyl acetate, followed by dropwise addition of 250 ml of normal-heptane over 30 minutes with stirring at room temperature, whereupon the objective compound crystallized out. The crystalline precipitate was collected by filtration, washed with 150 ml of an ethyl acetate-normal-heptane (1:1) mixture and then dried in vacuo to give 57.9 g of crude crystals containing 45.7 g of bicozamycin benzoate (yield: 77.6%).

(2) Process of this invention (benzoic anhydride process):

A 300-ml three-necked flask was charged with 55 ml of pyridine and 0.91 g of 4-dimethylaminopyridine. After dissolution of the latter, 22.4 g (on the pure substance basis) of bicozamycin was added, and the mixture was stirred at room temperature for about 30 minutes to complete dissolution of bicozamycin and then cooled to 0° to 5° C. Benzoic anhydride (36.9 g) was added, and the reaction was allowed to proceed for 2 hours with stirring at 15° to 20° C. and then terminated by adding 2.5 g of methanol and stirring for 20 minutes (% formation of the objective compound: 97.9%). The reaction mixture was transferred to a 500-ml three-necked flask and diluted with 125 ml of ethyl acetate. Thereafter, 75 ml of normal-heptane was added at room temperature and the mixture was stirred for 1 hour, whereupon the objective compound crystallized out. Then, 175 ml of normal-heptane was added dropwise over 30 minutes and the mixture was further stirred for 1 hour. The crystalline precipitate was collected by filtration, washed in sequence with 50 ml of an ethyl acetate-normal-heptane (1:1) mixture and 7.5 ml of water, and dried in vacuo to give 34.5 g of crude crystals containing 26.8 g of bicozamycin benzoate (yield: 89.0%).

As shown above, the process of this invention could improve the yield of bicozamycin benzoate by a little more than 10% as compared with the prior art process.

The following example is further illustrative of this invention.

EXAMPLE

A 300-ml three-necked flask was charged with 55 ml of pyridine and 0.91 g of 4-dimethylaminopyridine. After dissolution of the latter, 22.4 g (on the pure substance basis) of bicozamycin was added, and the mixture was stirred at room temperature for about 30 minutes to complete dissolution and then cooled to 0° to 5° C. Benzoic anhydride (36.9 g) was added, and the reaction was allowed to proceed for 2 hours with stirring at 15° to 20° C. and then terminated by adding 2.5 g of methanol and stirring for 20 minutes. The reaction mixture was transferred to a 500-ml three-necked flask and diluted with 125 ml of ethyl acetate. Thereafter, 75 ml of normal-heptane was added at room temperature and the mixture was stirred for 1 hour, whereupon the objective compound crystallized out. Then, 175 ml of normal-heptane was added dropwise over 30 minutes and the mixture was further stirred for 1 hour. The crystalline precipitate was collected by filtration, washed in sequence with 50 ml of an ethyl acetate-normal-heptane (1:1) mixture and 7.5 ml of water, and dried in vacuo to give 34.5 g of crude crystals of the objective compound.

A 200-ml three-necked flask was charged with 48 ml of isopropanol and 72 ml of water and then charged with 30.0 g of the above crude crystals at room temperature, followed by 10 minutes of stirring for dissolution of the latter. The solution was filtered for clarification and the 200-ml three-necked flask and the filter were washed with 30 ml of water, the washings being allowed to flow into the filtrate. The filtrate and washings thus collected in a 500-ml three-necked flask were cooled to 0° to 5° C. To the 500-ml three-necked flask were added 30 mg of seed crystals with stirring. The flask contents were stirred at 0° to 5° C. for 1 hour, whereupon the objective compound crystallized out. Then, 150 ml of water cooled to 0° to 5° C. was added dropwise to the flask over 30 minutes, followed by 4 hours of stirring. The resultant crystalline precipitate was collected by filtration, washed with 90 ml of water cooled to 0° to 5° C., and dried in vacuo to give 20.6 g of bicozamycin benzoate.

1) IR (paste method): 3250, 1712, 1683, 1284, 1117, 1072, 715 cm$^{-1}$

2) MASS: 407 [M+H$^+$]

3) NMR δ (ppm, DMSO-d$_6$): 1.37 (3H, singlet), 2.3–2.7 (2H, multiplet), 3.0–3.9 (2H, multiplet), 4.04 (1H, doublet), 4.26, 4.37 (2H, AB-type quartet), 5.07 (1H, doublet), 5.40 (1H, doublet), 5.66 (1H, doublet), 5.95 (1H, singlet), 6.90 (1H, singlet), 7.56 (2H double doublet), 7.69 (1H, double doublet), 8.01 (2H, double doublet), 8.77 (2H, singlet)

Based on the above physical properties and other data, the product was found to be identical with an authentic sample of bicozamycin benzoate.

INDUSTRIAL APPLICABILITY

As stated hereinabove, the process for producing bicozamycin benzoate according to this invention can markedly improve the yield of bicozamycin benzoate as compared with the prior art process and has a great merit in achieving a cost reduction in the commercial production thereof.

We claim:

1. A process for producing bicozamycin benzoate which comprises reacting bicozamycin with benzoic anhydride in the presence of 4-dimethylaminopyridine to yield bicozamycin benzoate.

2. A process for producing bicozamycin benzoate which comprises reacting bicozamycin with benzoic anhydride in pyridine in the presence of 4-dimethylaminopyridine to yield bicozamycin benzoate.

* * * * *